(12) United States Patent
Sambusseti

(10) Patent No.: US 9,433,509 B2
(45) Date of Patent: Sep. 6, 2016

(54) FLEXIBLE SURGICALLY IMPLANTABLE DEVICE, MADE OF COATED SILICONE, FOR JOINING PHALANXES, METACARPUS-PHALANX OR METATARSUS-PHALANX BONES IN ARTHROPLASTY SURGERY

(76) Inventor: Antonio Sambusseti, Cremona (IT)

( * ) Notice: Subject to any disclaimer, the term of this patent is extended or adjusted under 35 U.S.C. 154(b) by 53 days.

(21) Appl. No.: 14/119,537

(22) PCT Filed: May 22, 2012

(86) PCT No.: PCT/EP2012/059517
§ 371 (c)(1),
(2), (4) Date: Nov. 22, 2013

(87) PCT Pub. No.: WO2012/160070
PCT Pub. Date: Nov. 29, 2012

(65) Prior Publication Data
US 2014/0107797 A1    Apr. 17, 2014

(30) Foreign Application Priority Data

May 26, 2011   (IT) ................ MI2011A0951

(51) Int. Cl.
*A61F 2/42*    (2006.01)
*A61F 2/30*    (2006.01)

(52) U.S. Cl.
CPC .......... *A61F 2/4241* (2013.01); *A61F 2/4225* (2013.01); *A61F 2002/30069* (2013.01); *A61F 2002/3098* (2013.01); *A61F 2002/30729* (2013.01); *A61F 2002/4228* (2013.01); *A61F 2002/4233* (2013.01); *A61F 2002/4243* (2013.01); *A61F 2002/4251* (2013.01); *A61F2310/0058* (2013.01); *A61F 2310/00574* (2013.01)

(58) Field of Classification Search
CPC ............... A61F 2/4241; A61F 2002/4243; A61F 2002/4246; A61F 2002/4248; A61F 2002/4251; A61F 2002/4256; A61F 2002/4258
See application file for complete search history.

(56) References Cited

U.S. PATENT DOCUMENTS 3,737,919 A  *  6/1973  Child ........................... 623/2.23
3,875,594 A  *  4/1975  Swanson ............... A61F 2/4241
                                                                 623/18.11

(Continued)

FOREIGN PATENT DOCUMENTS

| EP | 0 042 808 A1 | 12/1981 |
| FR | 2 928 827 A1 | 9/2009 |
| GB | 2 043 452 A | 10/1980 |

OTHER PUBLICATIONS

International Search Report, dated Jun. 29, 2012, from corresponding PCT application.

*Primary Examiner* — Yashita Sharma
*Assistant Examiner* — Daniel Bissing
(74) *Attorney, Agent, or Firm* — Young & Thompson

(57) ABSTRACT

A surgically implantable device (1,10) made of a single piece of silicone, for joining phalanxes, metacarpus-phalanx or metatarsus-phalanx bones of the hand or foot in arthroplasty surgery, includes an enlarged central portion (2) formed by a thickened portion (5) having a rounded profile and provided with a canal (6) extending transversally in which a depression (7) is centrally formed, and by two elongated stem portions (3,4) which extend from the enlarged central portion (2), one opposed to the other. The device (1,10) is coated completely with at least one layer of turbostratic pyrolytic carbon less than or equal to 10 microns thick obtained by physical vapour deposition (PVD).

10 Claims, 3 Drawing Sheets

(56) References Cited

U.S. PATENT DOCUMENTS

| | | |
|---|---|---|
| 4,367,562 A | 1/1983 | Gauthier |
| 5,037,442 A * | 8/1991 | Wintermantel ..... A61F 2/30965 433/173 |
| 6,319,284 B1 | 11/2001 | Rushdy et al. |
| 2006/0129225 A1* | 6/2006 | Kopia et al. ................. 623/1.13 |
| 2008/0319460 A1* | 12/2008 | Cortellini ............. A61F 2/0063 606/151 |

* cited by examiner

FIG. 7
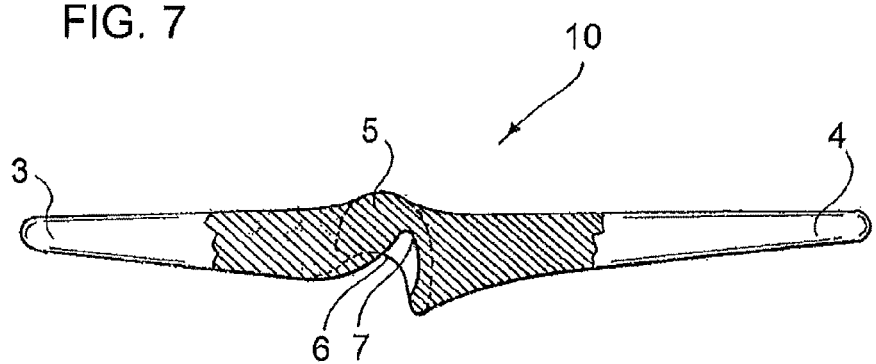
FIG. 8
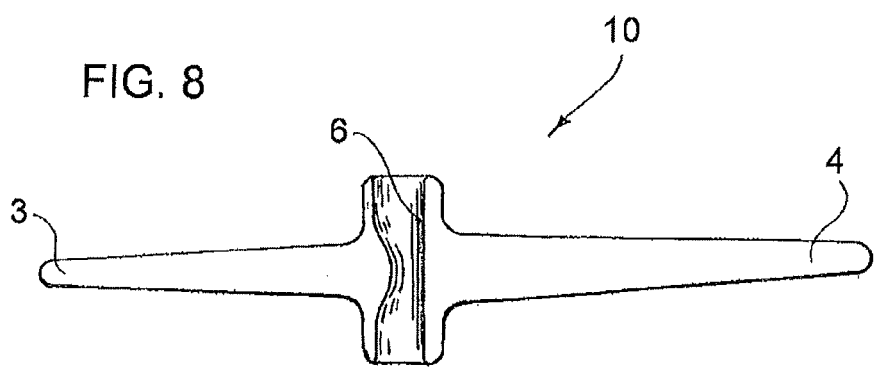
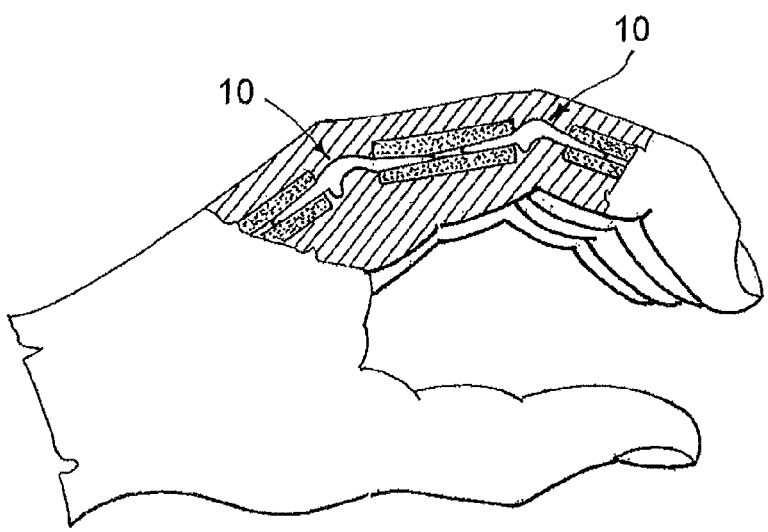
FIG. 9

FLEXIBLE SURGICALLY IMPLANTABLE DEVICE, MADE OF COATED SILICONE, FOR JOINING PHALANXES, METACARPUS-PHALANX OR METATARSUS-PHALANX BONES IN ARTHROPLASTY SURGERY

The present invention relates to a flexible surgically implantable device, made of coated silicone with an ultra-thin layer of turbostratic pyrolytic carbon for joining phalanxes, metacarpus-phalanx or metatarsus-phalanx bones in arthroplasty surgery.

Hands and/or feet can be affected by deforming diseases such as arthritis or rheumatoid arthritis, or be subject to traumatic episodes or post-traumatic arthritis, which cause the deformation of one or more phalanxes in relation to the others.

These deformations are very often incapacitating for the patient, very often resulting in difficulties in day-to-day life.

In these cases it is therefore desirable to restore the original shape and function of the hand or foot by carrying out surgery which involves the insertion, in the endomedullary canal of respective bones between two adjacent phalanxes or between a phalanx and a metacarpus, of a connecting joint to enable the original realignment of the phalanxes as well as their normal flexion.

Joints of various sizes, depending on their use, and various types are currently available on the market.

The first type is a flexible joint with a central hinge, formed in a single piece made of silicone, essentially used as a device for the phalanxes of the hand. This joint has the advantage of being extremely flexible, can be inserted into the spongy bone without damaging it and is capable of almost exactly reproducing the behaviour of the natural joints between the phalanxes, but suffers from the drawback of not being long-lasting as it tends to crumble after numerous flexion cycles, particularly when there are superficial lacerations on the joint caused by rubbing against the roughness of the spongy bone during insertion.

An improvement of the above-mentioned silicone joint is represented by a silicone joint that has two frusta-conical metal sleeves to be fitted into the respective intramedullary canals and positioned near the hinge, once the silicone joint has been inserted into said intramedullary canals. See, for example, the protected joint described for example in GB 2 043 452 relating to a device for the phalanxes of the hand.

Another type of joint is represented by a rigid two-piece joint composed of pyrolytic carbon.

This joint has the advantage of being more resistant to wear and flexion cycles but has the drawback of being more rigid than the spongy bone so that its insertion can damage the bone itself, particularly when said bone is thin because it is atrophied.

Furthermore, this material is very costly given the particular manufacturing process involved: in fact pyrolytic carbon, also called pyrocarbon, is obtained from a substrate of graphite heated at high pressure to temperature of 1400° C. in a special oven.

Patent application FR 2928827 describes rigid orthopaedic prostheses made of graphite coated with a film of pyrolytic carbon having a thickness of 300-600 microns obtained by Chemical Vapour Deposition (CVD).

However, a pyrolytic carbon film thus obtained is unsuitable for application on silicone joints to be inserted into the intramedullary canals of the bones of the hands and feet because it would cause the said joint to be stiff, in view of the joint's small dimensions.

The aim of the present invention is to eliminate, at least in part, the drawbacks of the known art, by providing a surgically implantable device for joining phalanxes, metacarpus-phalanx or metatarsus-phalanx bones in arthroplasty surgery which has substantially the same elasticity and flexibility as known silicone joints but is resistant to rubbing against the roughness of the spongy bone during insertion, which prevents breakage of the spongy bone during its insertion and which is long-lasting so as to avoid further surgical operations.

Another aim is to provide such a device which is cost-effective, easy to make and reliable.

These aims are achieved by a silicone device coated with turbostratic pyrolytic carbon having the characteristics listed in the accompanying independent claim 1.

Advantageous embodiments of the invention are described in the dependent claims.

The device according to the invention is a joint for joining phalanxes, metacarpus-phalanx or metatarsus-phalanx bones, made in one piece of a flexible, elastic and inert material, such as silicone, and is completely coated by at least one thin layer, also referred to herein as microfilm, of turbostratic pyrolytic carbon or diamond-like amorphous carbon, preferably turbostratic pyrolytic carbon, having a thickness lower than or equal to 10 microns.

The thickness of said coating is preferably in the order of about 0.2-0.3 microns although this range is not binding for the purposes of the present invention.

Said coating may be applied in a single layer or in a plurality of layers such as to achieve the desired thickness.

The application of said layer of turbostratic pyrolytic carbon or diamond-like amorphous carbon is achieved using known methods in order to obtain high-purity ultrathin films in the order of a few microns, for example using Physical Vapour Deposition method (PVD), particularly by adopting the "sputtering method".

In these physical deposition methods an atomic or molecular deposition occurs of a few tens or hundreds of nanometres thick on a substrate (the part to be coated).

The PVD technique involves transferring the carbon atoms from a turbostratic pyrolytic carbon element to the substrate to be coated, controlling the speed of deposition so as to obtain ultrathin films and operating under high-vacuum conditions at a constant temperature so as to prevent any chemical reaction.

The application of such a thin layer of pyrolytic carbon in turbostratic form ensures that no change in the physical and mechanical characteristics of the silicone occurs, particularly as regards its flexibility and elasticity.

Furthermore, the application of such a thin layer enables substantially the same morphology and dimensions as the known uncoated silicone joints to be maintained, thus achieving substantially the same elasticity and flexibility that such joints feature.

In fact, with coatings in the order of 300-600 microns thick obtained by means of CVD, like those of the prior art applied on other types of orthopaedic prostheses, the device of the present invention would be more rigid than the silicone, to the detriment of its flexibility and elasticity and therefore of its performance as a joint.

Furthermore, in the case of devices for joining phalanxes, metacarpus-phalanx or metatarsus-phalanx bones, where the dimensions of the device and cavity into which said device is to be inserted are small, it is extremely important to have coatings of the minimum thickness possible.

Further characteristics of the invention will emerge more clearly from the following detailed description, relating to one of its embodiments given purely by way of example and therefore not limiting, illustrated in the accompanying drawings, in which.

Figure 3:
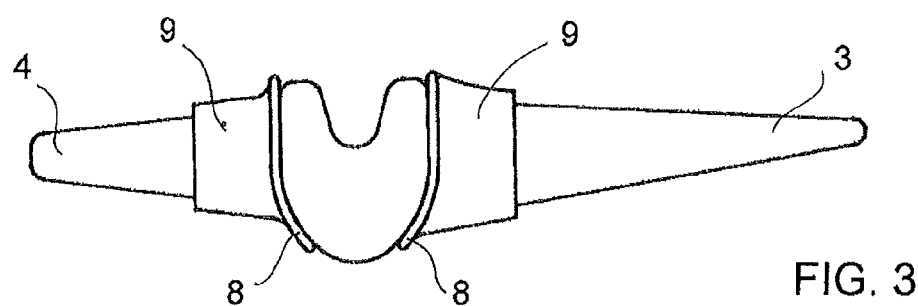
FIG. 3 is a side view of the device of FIG. 1 provided with reinforcing elements.
Figures 4A, 4B:
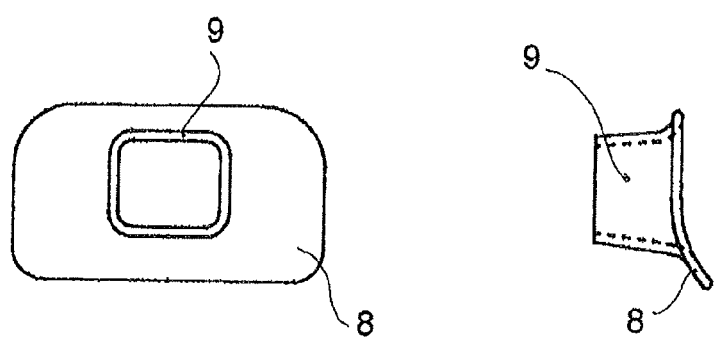
Figure 5:
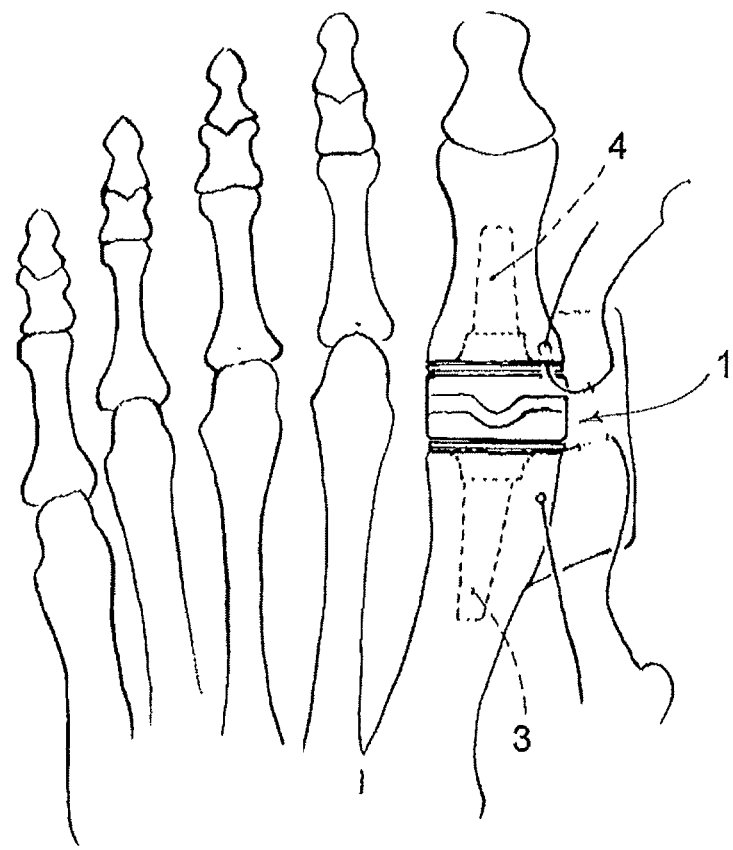
Figure 6:
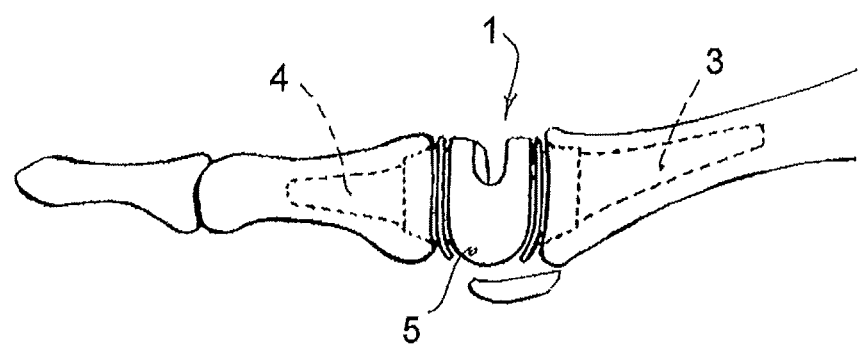

FIGS. 4 a) and b) are a front view and a side view respectively of a reinforcing element for the device of FIG. 3;

FIG. 5 is a top plan view of the phalanxes of a foot into which the device of FIG. 3 of the present invention has been inserted;

FIG. 6 is a side view of the phalanxes of FIG. 5 into which the device of FIG. 3 of the present invention has been inserted;

FIG. 7 is a partially cutaway side view of a device for the phalanxes of a hand according to the invention;

FIG. 8 is a bottom plan view of the device of FIG. 7;

FIG. 9 is a sectional view of a hand into which two devices of the present invention have been inserted.

An device according to the present invention, indicated in the Figures by the reference numeral 1, designed to be implanted in the phalanxes of the foot, will be described with reference to FIGS. 1-6.

Said device 1 is made in a single piece having a body formed by an enlarged central portion 2 from which extend, in opposite directions, two elongated stem portions 3 and 4, having a small cross section and tapered ends.

Said elongated portions 3 and 4 are designed to be inserted into respective intramedullary canals in the phalanxes of the foot and so have different lengths.

The enlarged central portion 2 comprises a thickened portion 5 having a rounded profile, the dorsal surface of which is continuous without depressions or cuts with a concavity upwards (or downwards if intended for the bones of the hand); said enlarged portion 2 also has a transverse channel 6 in which a depression 7 is centrally formed.

The enlarged central portion 2, and in particular the thickened portion 5, acts as a hinge and the depression 7 enables the maximum approach of the two stems 3 and 4 when the phalanxes into which the device 1 has been inserted are bent.

As illustrated in FIGS. 1-6, the thickened portion 5 is located in the lower surface of the enlarged portion 2 when the device 1 is designed to be inserted into the phalanxes of the foot, whereas it is located in the upper part if the device 1 is to be inserted into the phalanxes of the hand, as shown in FIGS. 7-9.

Figure 1:
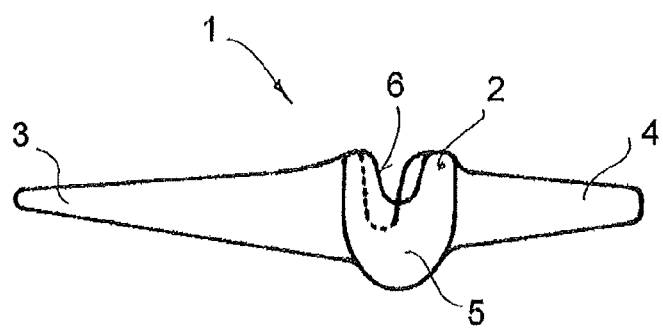
FIG. 1 is a side view of a device for the phalanxes of a foot according to the invention in the position of use.
Figure 2:
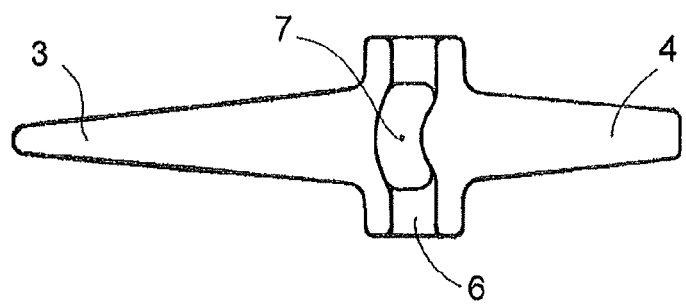
FIG. 2 is a top plan view of the device of FIG. 1.

Furthermore, if the device 1 is to be inserted into the foot, one of its two elongated portions 3, 4 is much shorter than the other, as shown in FIGS. 1 and 6, since the dimensions of these stems 3 and 4 substantially correspond to the dimensions of the intramedullary canals of the phalanxes of the foot into which they are to be inserted.

In devices 1 intended for the bones of the foot, the use of metal reinforcing plates 8 having a sleeve 9 is particularly preferred, in view of the greater stress to which this device 1 is subjected due to the weight of the body.

Into said plates 8 the two elongated portions 3 and 4 will then be inserted, as illustrated in FIG. 3.

Referring to FIGS. 7-9, the device of the present invention for insertion into the bones of the hand, indicated by reference numeral 10, is substantially similar to the device 1 for the foot, but the thickened portion 5 having the rounded profile is located in the upper surface of the enlarged portion 2, having the concavity of the dorsal surface of the thickened area 5 facing downwards. Furthermore, the extensions 3 and 4 have substantially the same rather than different lengths.

The device 10 for the bones of the hand can also be provided with reinforcing plates 8 although these are not necessary for the device 1 intended for the bones of the feet.

It is understood that the enlarged central portion 2 and/or the thickened portion 5 can also be made in different shapes to those shown in the above-mentioned Figures, provided that they act as a hinge for the joint 1 and 10.

Said device 1, 10 is obtained by means of molding medical silicone in various sizes and then coated with pyrolytic turbostratic carbon according to the known art previously described.

In practice said device 1, 10 is inserted into the intramedullary cavities of the phalanxes and/or metacarpus and/or metatarsus bones, previously prepared using appropriate instruments to enable the two stems 3 and 4 to be accommodated.

Thanks to the application of pyrolytic turbostratic carbon by means of PVD, it has been possible to obtain joints for joining phalanxes, metacarpus-phalanx or metatarsus-phalanx bones which substantially have the same high elasticity and flexibility as known silicone joints but have greater resistance to rubbing against the roughness of the spongy bone.

In practice the pyrolytic carbon is applied using the CVD method whereas the pyrolytic carbon in turbostratic form is applied using the PVD method as this allows layers that are 1000 times thinner to be obtained, so as to enable the mechanical properties of the substrates to remain unchanged.

The Applicant has found, through in depth studies, that the application of a pyrolytic turbostratic carbon microfilm on the surface of a device for joining phalanxes, metacarpus-phalanx or metatarsus-phalanx bones, made of silicone, enables a connecting joint to be obtained that does not crumble during its insertion into the intramedullary canals of the phalanxes as a result of rubbing against the internal roughness of said canals.

In particular, the Applicant has found that said pyrolytic turbostratic carbon coating remains unchanged over time also because it is highly resistant to body fluids such as blood, urine and the like.

Furthermore, tests conducted by the Applicant have shown that this pyrolytic turbostratic carbon coating remains applied to the surface of the silicone joint even after several flexion cycles of the device: therefore it is highly reliable, as well as easy to make, and not very expensive.

It should be noted that this turbostratic pyrolytic carbon microfilm has proved to be suitable for maintaining the flexibility of the underlying flexible silicone support since it is flexible too.

In the light of the above, the device of the present invention has numerous advantages such as a long life since it does not tend to crumble after numerous flexion cycles;

a resistance to the rubbing against the roughness of the spongy bone during insertion;

flexibility and softness such as not to damage the intramedullary canals of the bone, particularly when said bone is thin because it is atrophied.

Several variations and modifications to detail can be made to the present embodiments of the inventions, within the capabilities of a person skilled in the art but falling within the scope of the invention expressed by the accompanying claims.

The invention claimed is:

1. A surgically implantable device for joining any of the group consisting of phalanxes, metacarpus-phalanx and metatarsus-phalanx bones of a hand or foot in arthroplasty surgery, comprising:

an inert, elastic and flexible silicone material, formed as a single piece, with an enlarged central portion formed by a thickened portion, a dorsal surface of said central portion being continuous without depressions or cuts and having a concavity upwards or downwards, and provided with a channel extending transversally in which a depression is centrally formed, and two elongated stem portions having a smaller transversal section and tapered ends, which extend from said enlarged central portion, one opposed to the other, said depression configured to permit the two elongated stem portions to approach during bending of said single piece, said enlarged central portion and/or said thickened portion configured to operate as a hinge during said approach; and a film of turbostratic pyrolytic carbon, provided, on an exterior surface of the single piece, having a thickness lower than or equal to 10 microns and formed by one or more layers each consisting of turbostratic pyrolytic carbon applied by sputtering Physical Vapour Deposition (PVD), said film being in direct contact with the inert, elastic and flexible silicone material, and said film being resistant to rubbing against a roughness of a spongy bone, and configured to remain applied to the exterior surface of the inert, elastic and flexible silicone material even after several flexion cycles of said device.

2. The device according to claim 1, wherein the film has a thickness of 0.2-0.3 microns.

3. The device according to claim 1, wherein the film is formed by a plurality of layers.

4. The device according to claim 1, wherein the thickened portion is placed on a lower surface of the enlarged portion.

5. The device according to claim 4, wherein the two elongated stem portions have different lengths.

6. The device according to claim 1, wherein the thickened portion is placed on an upper surface of the enlarged portion.

7. The device according to claim 6, wherein the two elongated stem portions have equal lengths.

8. The device according to claim 1, wherein two reinforcing metal plates are provided, each of them having a sleeve to be fitted around a respective elongated stem portion.

9. The device according to claim 2, wherein the film is formed by a plurality of layers.

10. The device according to claim 1, wherein he single piece is completely coated with the film of turbostratic pyrolytic carbon, and said turbostratic pyroiytic carbon is directly in contact with the silicone of said single piece.

* * * * *